United States Patent [19]

Soldner

[11] 4,128,012
[45] Dec. 5, 1978

[54] ULTRASONIC EXAMINATION APPARATUS OPERATING ACCORDING TO THE IMPULSE-ECHO METHOD

[75] Inventor: Richard Soldner, Erlangen, Germany

[73] Assignee: Siemens Aktiengesellschaft, Berlin & Munich, Germany

[21] Appl. No.: 846,161

[22] Filed: Oct. 27, 1977

[30] Foreign Application Priority Data

Nov. 8, 1976 [DE] Fed. Rep. of Germany ....... 2651001

[51] Int. Cl.² ............................................. G01N 29/00
[52] U.S. Cl. ......................................... 73/611; 73/620; 128/2 V
[58] Field of Search ................. 73/610, 611, 613, 614, 73/615, 618, 620, 625; 128/2 V, 2.052; 358/112

[56] References Cited

U.S. PATENT DOCUMENTS

| | | | |
|---|---|---|---|
| 2,682,766 | 7/1954 | van Valkenburg | 73/611 |
| 3,914,987 | 10/1975 | Bickel et al. | 73/610 |
| 3,974,682 | 8/1976 | Soldner et al. | 128/2 V |

Primary Examiner—Stephen A. Kreitman
Attorney, Agent, or Firm—Hill, Gross, Simpson, Van Santen, Steadman, Chiara & Simpson

[57] ABSTRACT

In an illustrated embodiment, a selective receiver receives a first echo impulse produced at the interface between the precursor water path and the subject under examination, as a measure of the precursor transit time ($T_v$). Thereafter, each transmit pulse is synchronized with the receipt of such echo impulse so that multiple echoes resulting from such echo impulse coincide in time with desired echo signals, and thus do not disturb the accuracy of the display. By way of example, a trigger stage may respond to the interface echo to directly trigger transmission of the next ultrasonic pulse. The trigger stage may also actuate a first monostable with a time interval corresponding to the nominal precursor transit time ($T_v$), a second monostable being triggered by the first monostable to establish the actual gating interval for receipt of the resultant interface echo signal. The gated interface echo signal may be compared with a standard level and any deviation used to control amplification of the receiver.

7 Claims, 3 Drawing Figures

ULTRASONIC EXAMINATION APPARATUS OPERATING ACCORDING TO THE IMPULSE-ECHO METHOD

BACKGROUND OF THE INVENTION

The invention relates to an ultrasonic examination apparatus operating according to the impulse-echo method, particularly intended for medical purposes, consisting of an ultrasonic transmitting/receiving system, the transmitter of which radiates ultrasonic impulses at specific time intervals via a precursor path disposed in front of the system; for example, a water precursor path, into the subject to be examined, as well as consisting of an echo-impulse imaging device, operated in dependence upon the transmit impulses, which forms an image of the echo impulses, arriving at the receiver in chronological succession, of each transmit pulse corresponding to the chronological sequence of their occurrence.

Apparatus of this type is used e.g. as so-called A-scan or B-scan apparatus in the examination of materials or in medical diagnosis in order to detect or form an image of internal body layer structures; for example images of sections through internal organs, or the like. Generally, cathode ray tubes are utilized in order to construct echo visual images, wherein, depending upon the applied instance (B-scan or A-scan), the electron beam of the tube is deflected in dependence upon the ultrasonic-transmit-impulses, either in linear fashion over the display screen or only periodically over its time axis, and where the image formation of the echo impulses takes place by means of trace unblanking or analogous vertical deflection of the electron beam in each instance pursuant to arrival of an echo impulse. The precursor path between the ultrasonic transmitting/receiving system and the subject to be examined (for example, the body of a patient) is intended, on the one hand, to make working in the remote zone of the system possible in which specific intensity ratios within the directional characteristic of the ultrasonic transmitter are present. On the other hand, however, the precursor path also serves the purpose of blocking out image-falsifying multiple echoes from the image range of the echo display. As is known, multiple echoes occur as a result of repeated reflection of real echoes within the precursor path, occasioned in particular by the high reflection factor of the boundary between the sonic head and the precursor path medium. The particularly strong echo of the boundary surface between the precursor path medium and the surface of the examination subject appears here primarily as an interference factor. The echoes reflected on the sonic head act as additionally radiated transmit impulses which still manifest sufficient energy so that they also are capable of triggering echoes in the interior of the subject. Multiple echoes produced in this fashion, however, occur at undefined locations in the echogram; for example, in the echo visual image, and thus produce non-real image points. In accordance with conventional practice, these multiple echoes have hitherto been capable of being blocked out by selecting the transit time of the impulses through the precursor path to be greater than the transit time of the echoes in the subject, with reference to the maximum subject depth. In such a case, the first multiple echo does not occur until after the arrival of the last real echo from the examination area; i.e., it, as well as the following additional multiple echoes, is not recorded. Thus, all multiple echoes, as is customary, fall into the precursor time of the following transmit impulse. The above described method functions extremely well as long as work is carried out with relatively low impulse repetition rates. However, for reasons of flicker-free representation of echo visual images, it is desirable to endeavor to work with an increased transmit impulse sequence rate; i.e., to keep the repetition time interval $T_s$ of the transmit pulses as brief as possible and thus utilize the precursor time $T_v$ of these impulses for the purpose of interposing an additional impulse series. However, in the case of apparatus operating according to this principle (for example, ultrasonic examination apparatus according to U.S. Pat. No. 3,902,357), any multiple echoes which may possibly occur can no longer be blocked out of the echogram. On the contrary, these multiple echoes continue to occur in the image in the form of interference echoes, and it is possible, in any case, to recognize them as such interference echoes during the transition from a fixed to a wobbled impulse sequence due to the locations in the echo visual image which vary with the wobbling frequency.

SUMMARY OF THE INVENTION

It is the object of the present invention to develop an ultrasonic examination apparatus of the type initially cited such that multiple echoes will no longer be able to exert a disruptive effect on the echo images even in the case of high line scanning frequencies.

In accordance with the invention, the object is achieved with the aid of an additional installation comprising a time measuring element for detecting the precursor time $T_v$ of each transmit impulse through the precursor path and a regulating, or adjusting element for adjusting the impulse sequence time $T_s$ of respective consecutive transmit impulses to the measured precursor time.

In conventional ultrasonic impulse apparatus, the impulse sequence $T_s$ of the transmit impulses is a constant which is fixedly adjusted, or adjustable, on the apparatus. Thus, the position of the multiple echoes in the image is given by the variable precursor time $T_v$ and the repeat time $T_s$ of the transmit impulses. However, if, in accordance with the invention $T_s = T_v$ is selected, the multiple echoes arising as a consequence of multiple reflection will precisely coincide with the associated real echoes of the examined structure of the following impulse series. Accordingly, even though they continue to occur, these multiple echoes are brought into coincidence with the real echoes with which they are associated and hence are no longer visible. In the framework of an advantageous embodiment of the invention, the adjustment of $T_s = T_v$ is achieved in the most precise fashion by triggering a transmit impulse through the first echo (skin echo or sheet echo) of the previous echo series. The result is a technically particularly simple realization of the time measuring installation and the adjustment element which can be used with particular advantage in cases wherein precursor paths of varying lengths, or flexible precursor stretches (water receptacle with sheet closure or seal) are utilized. In this instance, with the simplest technical means and with particular speed, an automatic adjustment of the sequence time $T_s$ of the transmit pulses to the precursor path results, said precursor path constantly changing due to the different curvature during emplacement on the examination subject.

Other objects, features and advantages of the invention will be apparent from the following detailed description taken in connection with the accompanying sheet of drawings.

DETAILED DESCRIPTION OF THE PREFFERED EMBODIMENTS

Figure 1:
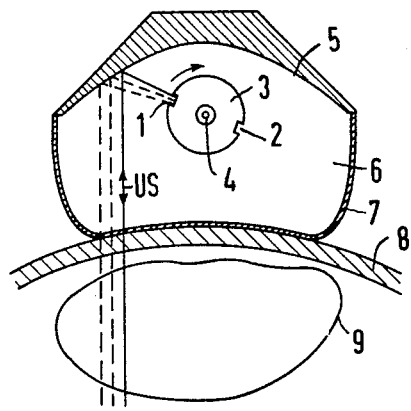
FIG. 1 illustrates the schematic construction of a preferred embodiment of an ultrasonic transmitting-/receiving system comprising a precursor path for an ultrasonic examination apparatus in accordance with the invention.

The applicator of FIG. 1 relates to a so-called rotary scanner comprising two ultrasonic transducer elements 1 and 2 (or more) which are arranged by means of a rotational carrier 3 in the focal axis 4 of a cylindrical parabolic reflector 5 such that they are rotatable about said focal axis. In the activated state, respectively, transducers 1 and 2 each produce an ultrasonic beam consisting of ultrasonic impulses which are transmitted in the direction of reflector 5 and which are reflected from the latter into the subject to be examined via a water coupling path provided by a medium 6 confined by a membrane sheet 7 which is permeable to ultrasound. In the present instance, the subject consists e.g. of a material abdomen with abdominal wall 8 and uterus 9 in which e.g. a fetus (non-illustrated) is located. When ultrasonic head assembly 1 through 3 is rapidly rotated, scanning by the ultrasonic beam US of the respectively activated ultrasonic transducer 1 or 2 takes place due to the reflection properties of reflector 5, said ultrasonic beam US scanning the subject (abdomen of the pregnant woman) in lines which are parallel to one another. The echo impulses originating from each ultrasonic scan line which are received by the particular ultrasonic transducer 1 or 2 active at that moment, and operating as transmitter and receiver, are finally reproduced as an image in linear form on the viewing screen of an oscillograph tube. There thus results the desired ultrasonic-echo-sectional image of the subject.

Figure 2:
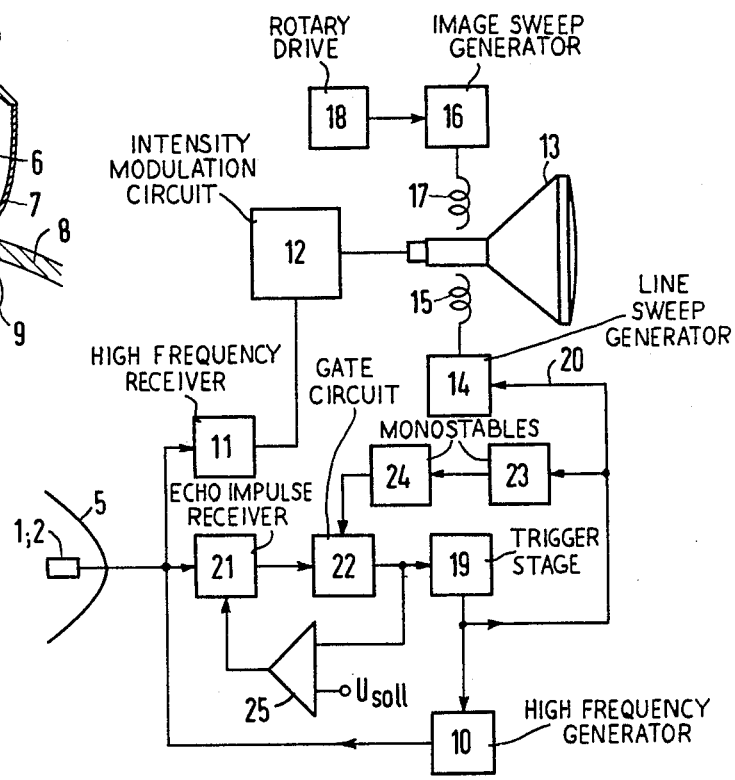
FIG. 2 illustrates a sample embodiment of the inventive ultrasonic examination apparatus in a basic circuit diagram comprising an ultrasonic transmitting/receiving system according to FIG. 1, as well as a cathode ray tube functioning as the imaging device for the echo impulses.

In the basic circuit diagram of FIG. 2, the sonic head of the transmitting/receiving system of FIG. 1 is only schematically illustrated at 1, 2. A high frequency generator for feeding the respective transducer is referenced with 10, and a first high frequency receiver for the echo signals is referenced with 11. The echo signals of the first receiver 11 are conveyed via an intensity modulation circuit 12 to the previously cited oscillograph tube 13 for the purpose of intensity modulation. In order to construct the line raster, there is a line sweep generator 14 in connection with the vertical deflection coil 15 and an image sweep generator 16 in connection with the horizontal deflection coil 17 of the oscilloscope tube 13. The image sweep generator 16 produces its image sweep voltage waveform in time-synchronism with the rotational movement of carrier 3 for the transducer elements 1 and 2 through a rotary drive 18. By way of contrast, the operation of line sweep generator 14 proceeds in dependence upon trigger signals of a trigger stage 19, e.g. a monostable multivibrator, via a trigger line 20. Trigger stage 19, in turn, is triggered in the cadence of the arrival of the respective first echo impulse (such as $TE_1$, FIG. 3, which is produced by a transmit pulse $S_1$) which may be received via a second echo impulse receiver 21 for this echo in addition to gate circuit 22 for the passage of only this echo to the trigger stage 19. With its output signal, trigger stage 19 triggers, in addition to the line sweep generator 14 of the oscillograph tube 13, the high frequency generator 10 for the ultrasonic-transmit impulses. In addition, trigger stage 19 also controls the position of the gate opening time of gate 22 relative to an expected first echo impulse. The control here proceeds via two monostable multivibrators 23 and 24. With each trigger impulse of trigger stage 19, the first monostable multivibrator 23 produces an output impulse having the duration of the precursor time $T_v$. The end flank (trailing edge) of this output signal, in turn, triggers the second monostable multivibrator 24, which determines the opening time of gate 22 with the duration of its output impulse. An amplitude control system for receiving amplifier 21 serves the purpose of producing echo impulses which are standardized as to their amplitude at the input of trigger stage 19. In the present instance, this amplitude control system comprises a differential amplifier 25 in an amplification feedback circuit of receiving amplifier 21. With its output signal, differential amplifier 25 regulates the degree of amplification of receiving amplifier 21 until the output signals of this amplifier correspond in amplitude to the nominal voltage value $U_{soll}$ connected to differential amplifier 25. In the sample embodiment of FIG. 2, separate receiving amplifiers 11 and 21, respectively, have been provided for the purpose of recording all echo signals, on the one hand, and for the purpose of receiving only the actual trigger echoes, on the other hand. However, it is certainly self-understood that only one single common receiving amplifier need be provided for both derivation operations. In the latter instance, there is control standardization of trigger echoes as well as all other echoes which are to be represented on the oscillograph viewing screen.

The mode of operation of the sample embodiment according to FIGS. 1 and 2 is apparent in connection with FIG. 3 as follows:

The sonic head 1, 2, transmits, in the manner described above, ultrasonic impulses US through the precursor stretch 6 with the precursor time $T_v$ into an examination area 8, 9 having the examination depth $T_u$. In FIG. 3, a first transmit impulse $S_1$ is illustrated which, given the prescribed configuration, produces e.g. the illustrated three echo impulses of an echo impulse line $E_1$ from the overall examination depth. The first echo $TE_1$ (trigger echo) is the sheet echo of the sheet membrane 7, i.e., the surface echo on the body surface 8 of the examination area. In FIG. 3, echo impulse $TE_1$ is assumed to be of such intensity that multiple echoes can be formed as a result of this inpulse. Since the precursor time $T_v$ amounts to double the transit time of a transmit pulse to the entry of the examination subject, these multiple echoes $ME_1$ occur at the end of the doubled precursor time $2 T_v$, weakened in their amplitude but nevertheless clearly visible. In a conventional apparatus embodiment, these multiple echoes $ME_1$ would appear in the echo visual image on the viewing screen of the oscillograph tube 13 in the form of non-real echoes; i.e., in the form of interference echoes, thus possibly giving rise to false diagnoses by virtue of their appearance. However, in accordance with the present invention, the respective first echo of a transmit impulse triggers the following transmit impulse; i.e., the impulse sequence time $T_s$ of two consecutive transmit pulses is adjusted to the precursor time, respectively. The instance illustrated in FIG. 3 thus results that the first echo $TE_1$ of transmit impulse $S_1$ directly triggers transmit impulse $S_2$ (and $TE_2$ triggers transmit impulse $S_3$, etc.). Since the real echoes $E_2$ resulting from this transmit impulse $S_2$, in turn, appear from the examination area time-delayed by the precursor time $T_v$, there results a precise overlapping (or coincidence) with the multiple echoes $ME_1$ of the first transmit impulse $S_1$. Hence, multiple echoes of a transmit impulse are always covered by real echoes of the following transmit impulse, so that they no longer become separately visible in the echo visual image as non-real interference echoes. As is clearly illustrated in FIG. 3, in the present sample embodiment, the echoes of a transmit impulse always lie within the precursor time of the following transmit impulse. As a consequence, there is a high line scanning frequency as well as image frequency without the interfering influence of multiple echoes on the video image representation.

Figure 3:
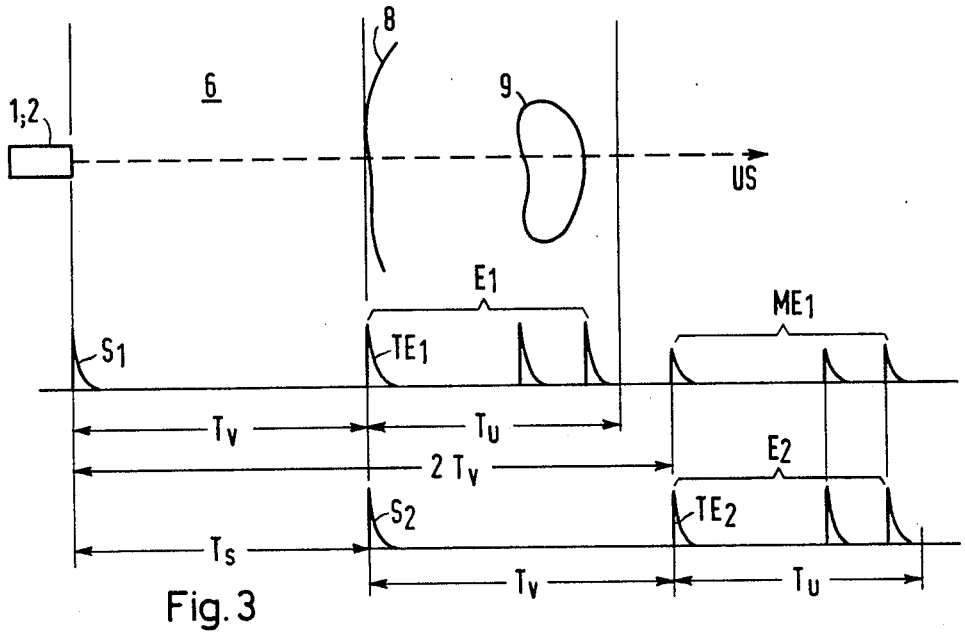
FIG. 3 illustrates a diagram of the sequence of transmit and echo impulses which can be adjusted with the apparatus according to FIG. 2.

Referring to FIG. 3, it will be understood that the electronic times such as $T_v$ and $T_s$ correspond to actual time intervals required for the illustrated echo signals such as $TE_1$ to be actually received by the receiver 11, 21 of FIG. 2. Thus, the spacial diagram at the upper part of FIG. 3 is to be understood as indicating the origin of the electronic pulses at the lower part of FIG. 3, but as will be apparent to those skilled in the art the time intervals at the lower part of FIG. 3 refer to the actual time up to receipt of the relevant signals by the receiver 11, 21. This is apparent since the monostable 23 is set to the minimum value of $T_v$ for a given ultrasonic examination subject, while monostable 24 is disclosed as defining the open time of gate 22, taking account the possible variation during the examination process for the particular subject. The electronic receiving gate 22 may comprise a logical AND member or an analog switch which is operative to trigger monostable 19 in response to an echo signal of the level determined by differential amplifier 25 and receiving amplifier 21.

It will be apparent that many modifications and variations may be effected without departing from the scope of the novel concepts and teachings of the present invention.

I claim as my invention:

1. Ultrasonic examination apparatus operating according to the impulse-echo method, particularly intended for medical purposes, comprising an ultrasonic transmitting/receiving system for radiating ultrasonic impulses into a subject to be examined, and having a precursor path through which the ultrasonic impulses are transmitted, an echo impulse imaging device, operated in dependence upon the transmit impulses, for forming an image of the echo impulses of each transmit pulse arriving at the receiver in chronological succession corresponding to the time sequence of their occurrence, characterized by an additional installation with a time measuring means (21 through 25) for determining the precursor time ($T_v$) of each transmit impulse through the precursor path (6), and an adjustment means (19) for adjusting the impulse sequence time ($T_s$) of respective consecutive transmit impulses to the measured precursor time.

2. Apparatus according to claim 1, characterized in that the time measuring means comprises a selective receiver means (21, 22, or 11, 22) for the respective first echo impulse of a transmit impulse which receiver means is coupled at its outlet side to the ultrasonic transmitter (1,2) for the purpose of triggering the following transmit impulse with the reception of the first echo of the preceding tansmit impulse, respectively.

3. Apparatus according to claim 2, characterized in that each received first echo impulse of a preceding transmit impulse itself actuates the trigger impulse for triggering the following transmit impulse.

4. Apparatus according to claim 2, characterized in that said receiver means (21, 22) has a trigger stage (19) coupled therewith such that each first echo impulse of a transmit pulse triggers the trigger stage (19) for producing a trigger impulse in order to trigger the following transmit impulse.

5. Apparatus according to claim 2, characterized in that the selective receiver means comprises a receiving amplifier (11 or 21) with an electronic receiving gate (22) for transmitting the respective first echo impulse.

6. Apparatus according to claim 5, characterized in that two monostables (23, 24) are connected in series, the selective receiver means (21, 22) having a trigger stage (19) connected to an input of a first of the two monostables, and the output of the second of the two monostables controlling the opening time of the gate (22) each time the first monostable (23) is triggered by a trigger impulse of the trigger stage (19), the first monostable (23) producing an output impulse of a duration representing the precursor time ($T_v$), and the other monostable (24) being triggered at the termination of this output impulse and producing an output impulse having the duration of the gate opening time.

7. Apparatus according to claim 2, characterized in that the selective receiver means includes an amplifier (21 or 11) with an amplification regulating feedback circuit adjustable to maintain a standard amplitude of the output signals therefrom.

* * * * *